US009290535B2

(12) United States Patent
Kim et al.

(10) Patent No.: US 9,290,535 B2
(45) Date of Patent: Mar. 22, 2016

(54) URIDINE-BASED GADOLINIUM COMPLEX AND MRI CONTRAST AGENT INCLUDING THE SAME

(75) Inventors: Jong-Seung Kim, Gyeonggi-do (KR); Sankarprasad Bhuniya, Seoul (KR); Sumin Lee, Seoul (KR); Kwan Soo Hong, Chungcheongbuk-do (KR); Hyunseung Lee, Chungcheongbuk-do (KR); Hyeyoung Moon, Chungcheongbuk-do (KR)

(73) Assignees: Korea University Researchand Business Foundation, Seoul (KR); Korea Basic Science Institute, Daejeon (KR)

( * ) Notice: Subject to any disclaimer, the term of this patent is extended or adjusted under 35 U.S.C. 154(b) by 31 days.

(21) Appl. No.: 14/004,831

(22) PCT Filed: Mar. 15, 2012

(86) PCT No.: PCT/KR2012/001864
§ 371 (c)(1),
(2), (4) Date: Sep. 12, 2013

(87) PCT Pub. No.: WO2012/128504
PCT Pub. Date: Sep. 27, 2012

(65) Prior Publication Data
US 2014/0005369 A1    Jan. 2, 2014

(30) Foreign Application Priority Data
Mar. 18, 2011    (KR) .................. 10-2011-0024292

(51) Int. Cl.
*C07F 5/00*    (2006.01)
*C07H 23/00*    (2006.01)
*A61K 49/10*    (2006.01)
*C07H 19/067*    (2006.01)

(52) U.S. Cl.
CPC .............. *C07H 23/00* (2013.01); *A61K 49/103* (2013.01); *C07F 5/003* (2013.01); *C07H 19/067* (2013.01)

(58) Field of Classification Search
None
See application file for complete search history.

(56) References Cited

PUBLICATIONS

Bhuniya et al., "Uridine-based Paramagnetic Supramolecular Nanoaggregate with High Relaxivity Capable of Detecting Primitive Liver Tumor Lesions," *Biomaterials*, vol. 32, Issue 27, Sep. 2011, pp. 6533-6540.
Camargo et al., "Synthesis, Structure, and Phosphatase-Like Activity of a New Trinuclear Gd Complex with the Unsymmetrical Ligand $H_3L$ as a Model for Nucleases," *Inorganic Chemistry*, vol. 49, No. 6, 2010, pp. 3057-3063.
Caravan, Peter, "Strategies for Increasing the Sensitivity of Gadolinium Based MRI Contrast Agents," *Chemical Society Reviews*, No. 35, Issue 6, 2006, pp. 512-523.
Lauffer, Randall B., "Paramagnetic Metal Complexes as Water Proton Relaxation Agents for NMR Imaging: Theory and Design," *Chemical Reviews*, vol. 87, No. 5, 1987, pp. 901-927.
Lee et al., "Uridine-Based Paramagnetic Supramolecular Nanoaggregate: a Liver Specific T1 MRI Contrast Agent High Relaxivity and pH Sensitivity," In: Abstract for Annual Meetings for Korean Chemical Society, Mar. 7, 2011.
Lee et al., "Uridine-Based Paramagnetic Amphiphiles: First Examples of Nucleoside-Based Potential T1 MRI Contrast Agent," In: Abstract for Annual Meetings for Korean Chemical Society, Sep. 9, 2010.
Mewis et al., "Biomedical Applications of Macrocyclic Ligand Complexes," *Coordination Chemistry Reviews*, vol. 254, Issues 15-16, Aug. 2010, pp. 1686-1712.
Naser et al., "Synthesis of Metal Ion Chelating Nucleosides," In: Abstract for Natural Science Symposium in Reykjavik, Iceland, Mar. 3, 2006.
Schuhle et al., "Calix[4]arenes as Molecular Platforms for Magnetic Resonance Imaging (MRI) Contrast Agents," *Chemistry—A European Journal*, vol. 15, Issue 13, Mar. 16, 2009, pp. 3290-3296.
Werner et al., "High-Relaxivity MRI Contrast Agents: Where Coordination Chemistry Meets Medical Imaging," *Angewandte Chemie International Edition*, vol. 47, Issue 45, Oct. 27, 2008, pp. 8568-8580.
Yam et al., "Recent Advances in Utilization of Transition Metal Complexes and Lanthanides as Diagnostic Tools," *Coordination Chemistry Reviews*, vol. 184, Issue 1, Apr. 1999, pp. 157-240.
International Search Report and Written Opinion for International Appl. No. PCT/KR2012/001864, mailed Oct. 24, 2012.

*Primary Examiner* — Michael G Hartley
*Assistant Examiner* — Melissa Perreira
(74) *Attorney, Agent, or Firm* — Alston & Bird LLP

(57) ABSTRACT

The present invention relates to a new uridine nucleoside-based amphiphilic gadolinium complex and a magnetic resonance imaging (MRI) contrast agent including the gadolinium complex. The MRI contrast agent has high relaxivity, high binding affinity for and stability in human serum albumin, pH response, and high liver specificity.

4 Claims, 14 Drawing Sheets

URIDINE-BASED GADOLINIUM COMPLEX AND MRI CONTRAST AGENT INCLUDING THE SAME

CROSS-REFERENCE TO RELATED APPLICATIONS

This application is a national stage application filed under 35 U.S.C. 371 of International Application No. PCT/KR2012/001864, filed Mar. 15, 2012, which claims priority from Korean Patent Application No. 10-2011-0024292, filed Mar. 18, 2011, each of which is incorporated by reference herein in its entirety.

TECHNICAL FIELD

The present invention relates to a new gadolinium complex and a magnetic resonance imaging (MRI) contrast agent including the same. More specifically, the present invention relates to a uridine-based MRI contrast agent that has high relaxivity, high binding affinity for and stability in human serum albumin, pH response, and high liver specificity.

BACKGROUND ART

Magnetic resonance imaging (MRI) is a powerful noninvasive technique that provides high quality three dimensional images of tissues, including information on anatomy, function, and metabolism of tissue in vivo.

The chelated $Gd^{3+}$ metal ion improves image contrast by decreasing the longitudinal relaxation time (T1) of proximal water protons, which appear brighter in the T1-weighted MR image. Current advanced medical diagnosis techniques stipulate high-resolution images with a high magnetic field scanner.

However, current $Gd^{3+}$-based contrast agents are incapable of meeting requirements as they do not have optimal relaxivity profiles at high magnetic fields. This requirement drives the research for smart contrast agents with high relaxivities (r1) for better tissue contrast at high magnetic fields and non-covalent binding affinity for human serum albumin (HSA) to enhance in vivo retention time in MR angiography applications.

In recent years, research has been conducted to develop contrast agents that have high pH sensitivity as well as meet the above requirements. pH sensitivity is a very important factor in in vivo mapping of living cells, particularly pathogenic cells.

Among the several approaches, the gadolinium complex into self-assembled nanoparticle system is one of the attractive approaches to develop high relaxivity contrast agent. In this system the high relaxivity achieved due to additive effect of self-aggregated Gd-complexed nuclei and slow global rotational motion.

Most of the gadolinium complexes reported to date have relaxivities lying between 20 and 25 $mM^{-1}s^{-1}$ at 20 MHz (0.47 T) in water at 25° C. Recently, Bota et. al. reported DOTA-based amphiphile with highest relaxivity of 34.8 $mM^{-1}s^{-1}$ at 25° C., 20 MHz (0.47 T) at pH 7.2.

There has recently been an increasing demand for pH-responsive contrast agents. Particularly, in in vivo pH mapping of tissues, pH-responsive contrast agents are very important in the diagnosis of cancers such as melanoma whose extracellular pH ($pH_e$) is lower by almost 0.6 than that of healthy subcutaneous tissue. However, to the best of our knowledge, MRI contrast agents have not yet been developed that have high relaxivity and meet requirements in terms of relaxivity, pH sensitivity, and stability.

DISCLOSURE

Technical Problem

It is an object of the present invention to provide a new uridine-based gadolinium complex that has high relaxivity, considerable binding affinity with human serum albumin, high pH sensitivity, and good stability, and a method for preparing the uridine-based gadolinium complex.

It is another object of the present invention to provide an MRI contrast agent including the uridine-based gadolinium complex that is effective to diagnose diseases, particularly liver abnormalities.

Technical Solution

The present invention provides a uridine-based gadolinium complex represented by Formula 1:

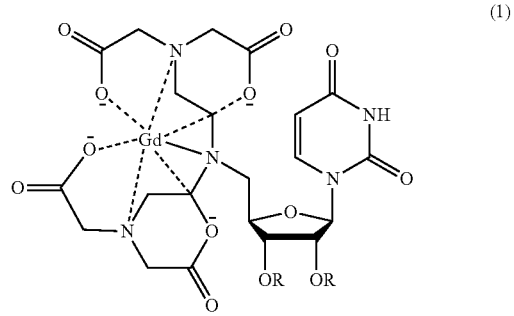

(1)

wherein each R is H or $CH_3(CH_2)_nCO$— where n is an integer from 1 to 12.

In one embodiment of the present invention, R is preferably $CH_3(CH_2)_nCO$— where n is at least 6, more preferably 8 (i.e. R=$CH_3(CH_2)_8CO$—).

The present invention also provides a ligand represented by Formula 2:

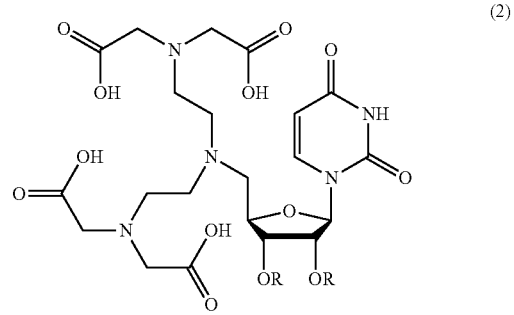

(2)

wherein each R is $CH_3(CH_2)_nCO$— where n is an integer from 1 to 12.

The present invention also provides a method for preparing a uridine-based gadolinium complex of Formula 1, as depicted in Scheme 1-1 or 1-2:

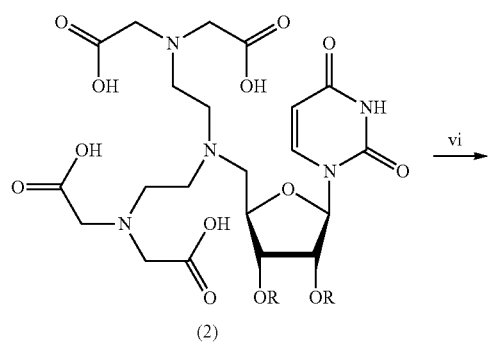

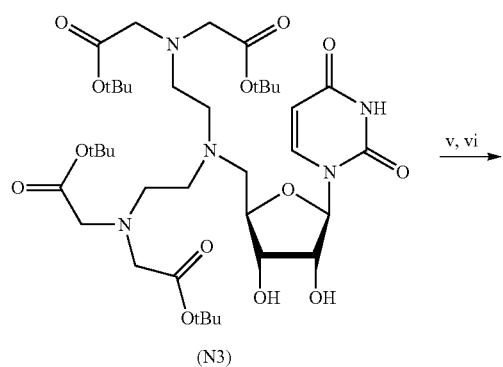

wherein vi represents GdCl$_3$·6H$_2$O, H$_2$O, and Na$_2$CO$_3$;

wherein v represents TFA and DCM, and vi represents GdCl$_3$·6H$_2$O, H$_2$O, and Na$_2$CO$_3$.

The present invention also provides a method for preparing a ligand of Formula 2, as depicted in Scheme 2:

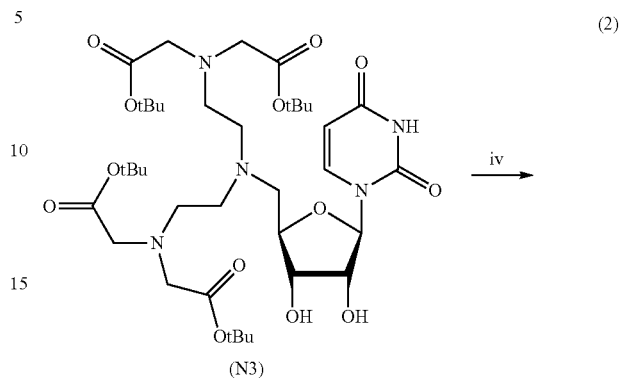

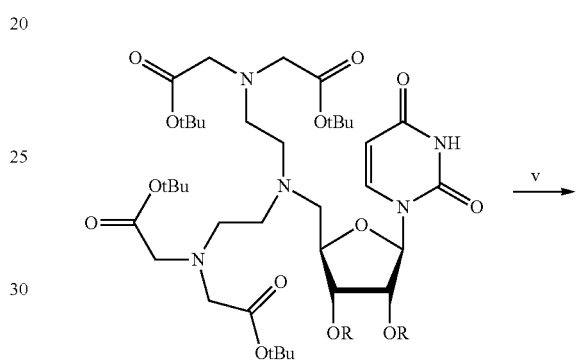

wherein iv represents RCO$_2$H, EDCI, DMAP, and DMF, and v represents TFA and DCM.

The compound of Formula N3 may be prepared by Scheme 3:

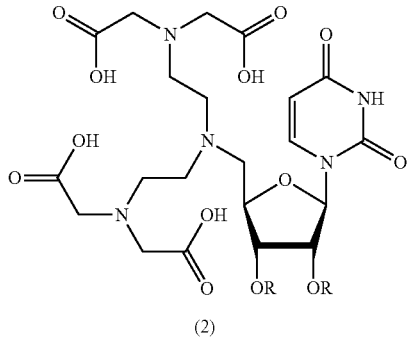

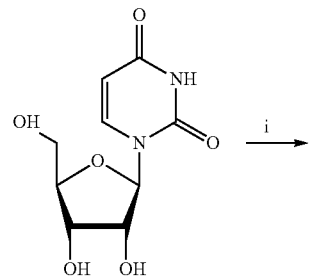

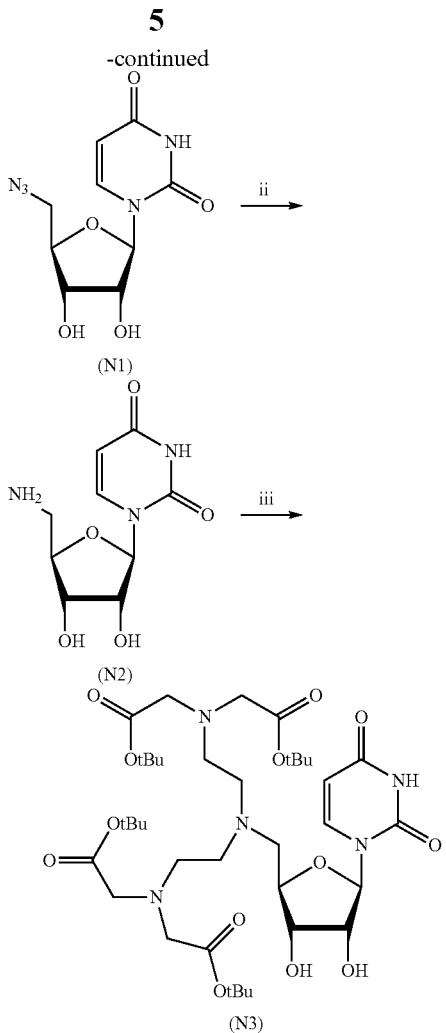

wherein i represents PPh$_3$, NaN$_3$, CBr$_4$, and DMF, ii represents PPh$_3$, pyridine then NH$_4$OH, and iii represents N,N-bis[(tert-butoxycarbonyl)methyl]-2-bromoethylamine, KHCO$_3$, and DMF.

The present invention also provides an MRI contrast agent including the uridine-based gadolinium complex of Formula 1. The contrast agent is effective in diagnosing liver abnormalities and may be prepared and used in the form of an intravenous injection.

Advantageous Effects

The uridine nucleoside-based amphiphilic gadolinium complex of the present invention can be utilized as an effective MRI contrast agent. The uridine-based gadolinium contrast agent of the present invention is the first self-assembled paramagnetic amphiphile with high relaxivity, significant binding ability with human serum albumin, pH response, and high liver specificity.

In addition, stability studies of the complex indicate that the new amphiphilic complex of the present invention is quite stable compared to commercially available Gd-DTPA and Gd-DTPA-BMA.

Furthermore, the pharmacokinetics of the new complex according to the present invention in animal experiments shows that the complex is highly specific for hepatocytes causing excretion into the bile ducts, gall bladder, and intestines. Therefore, the complex of the present invention may be a highly potential T$_1$ contrast agent to provide with detection of small lesions in the liver. The new uridine-based amphiphilic contrast agent represents an important and highly efficient nanosystem for MRI applications.

MODE FOR INVENTION

Figure 1:
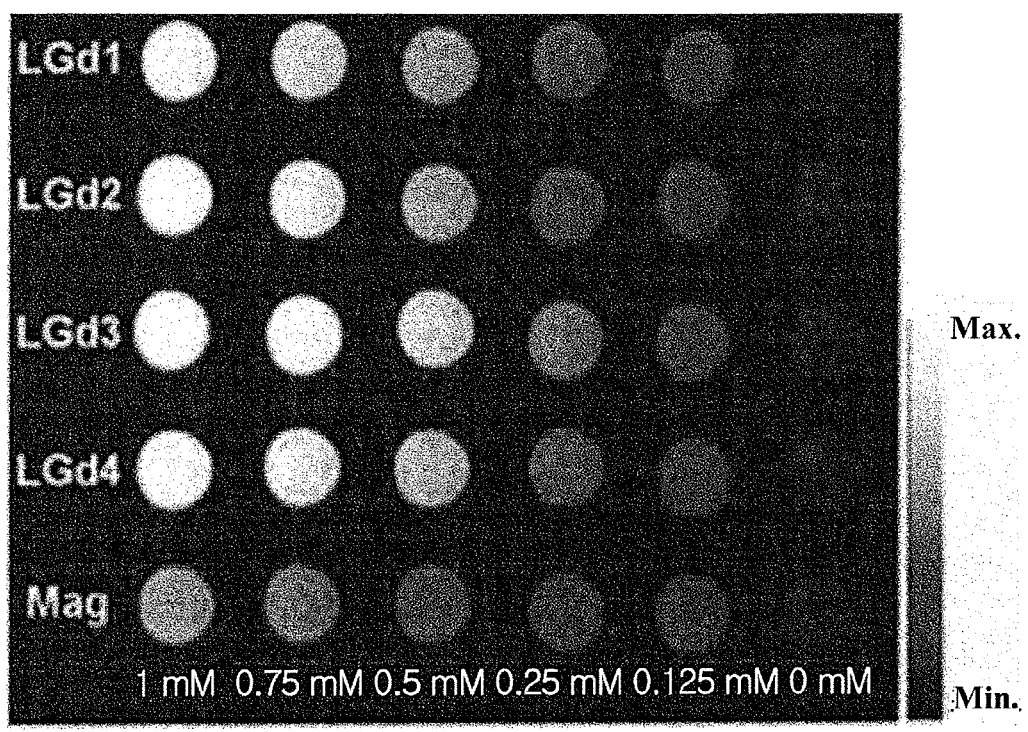
FIG. 1 shows a T$_1$-weighted spin-echo MR image (FOV=7 cm; matrix=256×256; TE/TR=11/100 ms; slice thickness=2 mm; number of acquisitions=50) for complexes LGd1-4 and Mag (Magnevist®, Gd-DTPA) in PBS solution at six different concentrations (1.0, 0.75, 0.5, 0.25, 0.125, and 0 mM) of the complexes at 63.8 MHz (1.5 T) and 36° C.

Embodiments of the present invention will now be described in more detail.

The present inventors synthesized nucleoside-based contrast agents. Nucleosides are already exploited for sophisticated biomaterials, including drugs and self-assembled materials. It is noteworthy that nucleosides inherently bind with protein, which may encourage contrast agent (CA) binding with human serum albumin (HSA).

To justify this speculation, the present inventors synthesized new uridine-based contrast agents (Formula 1) in a simple and economical manner in the present invention, as depicted in the following scheme.

First, amphiphilic ligands L1-4 (Formula 2) necessary for the synthesis of the contrast agents according to the present invention were obtained through four successive steps. Complexation was carried out in aqueous media at a pH of about 7 and afforded the anionic complexes LGd1-5 (Formula 1) of the present invention.

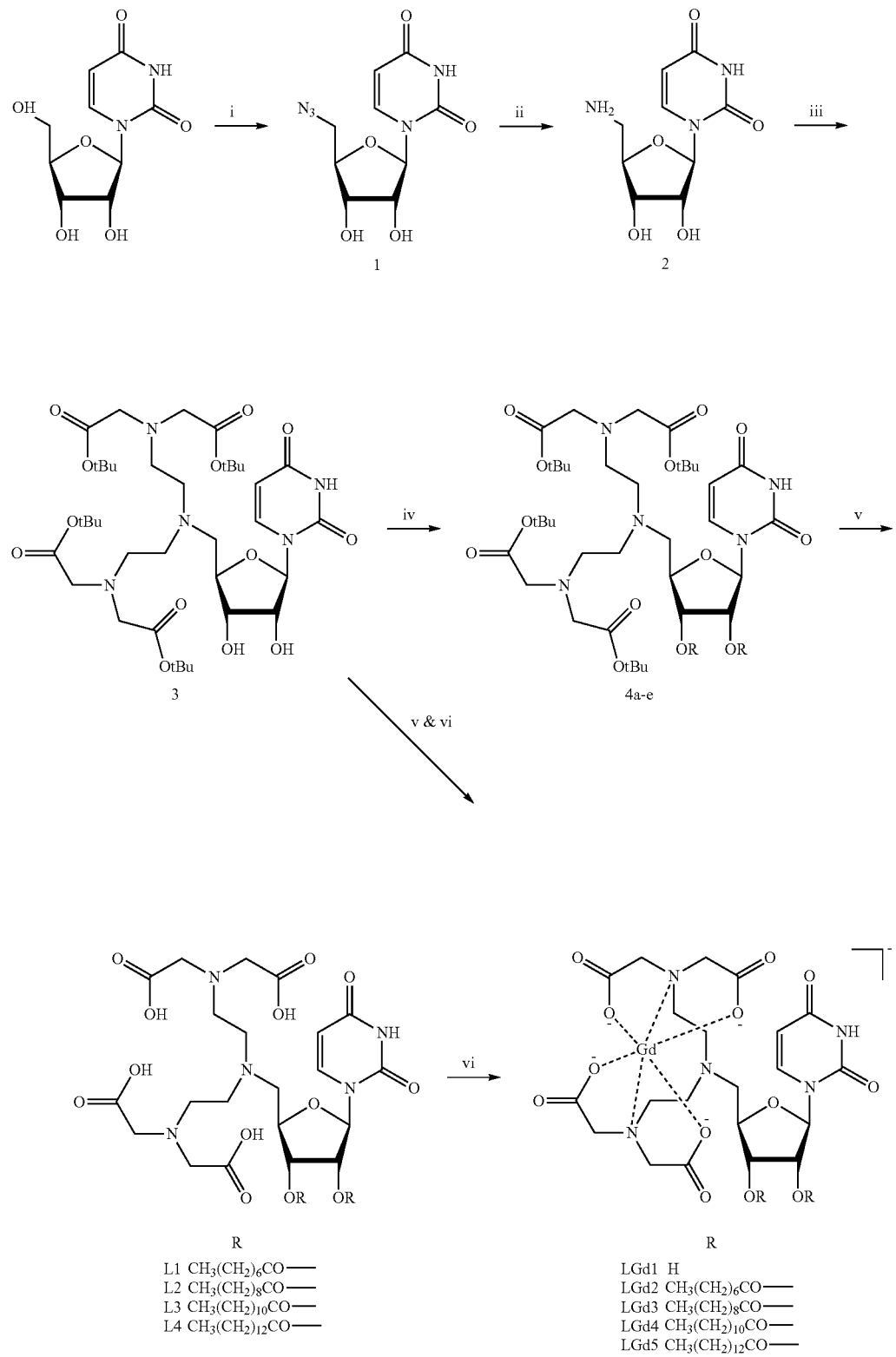

L1 CH$_3$(CH$_2$)$_6$CO—
L2 CH$_3$(CH$_2$)$_8$CO—
L3 CH$_3$(CH$_2$)$_{10}$CO—
L4 CH$_3$(CH$_2$)$_{12}$CO—

LGd1 H
LGd2 CH$_3$(CH$_2$)$_6$CO—
LGd3 CH$_3$(CH$_2$)$_8$CO—
LGd4 CH$_3$(CH$_2$)$_{10}$CO—
LGd5 CH$_3$(CH$_2$)$_{12}$CO—

Poly(aminocarboxylate) groups were selected in the present invention in order to ensure sufficient thermodynamic stability of the $Gd^{3+}$ complexes. Thermodynamic stability is an important factor in terms of in vivo stability. The amphiphilicity of the contrast agents is of great significance in that they induce self-assembly, which plays a crucial role in significantly reducing the molecular tumbling.

On the other hand, 1,3-diaxial steric-interactions between the C5 sugar (ribose) and the bulky ligand of 1'-uricyl group may restrict the local rotational motion of the $Gd^{3+}$ chelate (represented by the correlation time $\tau_{R1}$) compared to the global rotation of the molecule.

The present invention will be explained in more detail with reference to the following examples. However, these examples are provided to assist in a further understanding of the invention and are not to be construed as limiting the scope of the invention.

Synthesis Example 1

Synthesis of Compounds of Formulae N1 and N2

5-Azido-5'-dioxyuridine (N1) was synthesized in a yield of 90% according to the method described in the previously reported literature (R. B. Lauffer, *Chem. Rev.* 1987, 87, 901). 5-Amino-5'-dioxyuridine (N2) was synthesized in a yield of 84% from 5-azido-5'-dioxyuridine according to the method described in the literature (P. Caravan, *Chem. Soc. Rev.* 2006, 35, 512). N,N-bis[(tert-butoxycarbonyl)methyl]-2-bromoethylamine (A) was synthesized in a yield of 83% according to the published literature (E. J. Werner, A. Datta, C. J. Jocher, K. N. Raymond, *Angew. Chem. Int. Ed.* 2008, 47, 8568).

Synthesis Example 2

Synthesis of the Compound of Formula N3

The compound of Formula N2 (486 mg, 2 mmol) and $KHCO_3$ (505 mg, 5 mmol) in anhydrous N,N-dimethylformamide (10 mL) were cooled to 0° C. A solution of N,N-bis[(tert-butoxycarbonyl)methyl]-2-bromoethylamine (A) (1.409 g, 4 mmol) in DMF (5 mL) was added drop wise over a period of 20 min. Then the reaction temperature was raised to room temperature and stirring was continued for 60 h. The reaction mixture was diluted with water and extracted with ethyl acetate (4×50 mL). The organic layer was dried over anhydrous magnesium sulfate and concentrated in vacuo. The crude compound was passed through silica gel column chromatography using methanol (3-5%) in methylene chloride as eluent and dried to afford 660 mg (41.98%) of the compound of Formula N3.

$^1$H-NMR (400 MHz, CDCl$_3$): δ 7.49 (d, 1H, J=8.12 Hz); 5.88 (d, 1H, J=2.80 Hz); 5.75 (d, 1H, J=8.12 Hz); 4.22 (q, 1H); 4.04 (dt, 2H, J=6.8 Hz); 3.50 (s, 8H); 2.98 (br, 8H); 2.55 (m, 2H); 1.47 (s, 36H). $^{13}$C-NMR (100 MHz, CDCl$_3$): δ 171.10, 170.44, 163.63, 150.64, 102.71, 82.01, 81.96, 81.88, 72.01, 56.41, 56.37, 53.52, 28.33 ppm. FAB-MS m/z (M+H) calcd. 786.44, found 786.10.

Synthesis Example 3

Synthesis of Compounds of Formula N4a-d

Carboxylic acid (2.5 mmol) was added to a solution of the compound of Formula N3 (1.0 mmol), EDCI (2.5 mmol) and DMAP (1.0 mmol) in dry DMF (10 mL). The mixture was stirred at room temperature for 6 h. The reaction mixture was diluted with water and extracted with ethyl acetate (3×50 mL). The organic layer was dried with anhydrous magnesium sulfate and concentrated in vacuo. The residue was passed through silica gel column chromatography using ethyl acetate/hexane (3:2) as eluent and dried to afford 660 mg (41.98%) of compounds of Formulae N4a-d.

Compound N4a: yield 780 mg (83.81%), colorless oil. $^1$H-NMR (400 MHz, CDCl$_3$): δ 10.24 (s, 1H); 7.79 (d, 1H, J=8.16 Hz); 6.17 (d, 1H, J=6.74 Hz); 5.80 (d, 1H, J=8.12 Hz); 5.53 (m, 2H); 4.19 (br, 1H); 3.44 (s, 8H); 3.16 (q, 1H); 2.80 (br, 9H); 2.38 (t, 2H, J=7 Hz); 2.25 (t, 2H, J=7.01 Hz); 1.64 (m, 2H); 1.55 (m, 2H); 1.44 (s, 36H); 1.33-1.22 (br, 16H); 0.88 (t, 3H, J=8.24 Hz). $^{13}$C-NMR (100 MHz, CDCl$_3$): 172.46, 172.07, 171.57, 166.24, 151.33, 143.31, 102.40, 85.92, 80.88, 72.11, 71.27, 55.60, 55.46, 50.79, 50.64, 34.06, 33.82, 31.71, 29.24, 29.06, 28.96, 28.24, 24.97, 24.72, 22.69, 22.65, 14.14 ppm. FAB-MS m/z (M+1) calcd. 1038.65, found 1038.54.

Compound N4b: yield 800 mg (73.12%), colorless oil. $^1$H-NMR (400 MHz, CDCl$_3$): δ8.21 (s, 1H); 7.76 (d, 1H, J=8.20 Hz); 6.09 (d, 1H, J=5.80 Hz); 5.79 (d, 1H. J=8.08 Hz); 5.49 (m, 2H); 4.19 (m, 1H); 3.43 (s, 8H); 3.15 (q, 1H); 2.87-2.67 (m, 8H); 2.64 (q, 1H); 2.35 (t, 2H, J=4.89 Hz); 2.25 (t, 2H, J=4.04 Hz); 1.62 (m, 2H); 1.52 (m, 2H); 1.44 (s, 36H); 1.34-1.25 (br, 24H); 0.88 (t, 3H, J=2.24 Hz). $^{13}$C-NMR (100 MHz, CDCl$_3$): δ 172.53, 172.15, 170.83, 163.63, 150.93, 140.80, 103.32, 86.14, 80.96, 71.94, 71.61, 56.00, 54.24, 52.93, 51.14, 34.12, 33.89, 31.98, 29.59, 29.38, 29.19, 25.03, 24.78, 22.79, 14.23 ppm. FAB-MS m/z (M$^+$) calcd. 1093.71, found 1093.70.

Compound N4c: yield 900 mg (78.02%), colorless oil. $^1$H-NMR (400 MHz, CDCl$_3$): δ 9.01 (s, 1H); 7.75 (d, 1H, J=8.16 Hz); 6.10 (d, 1H, J=6.01 Hz), 5.78 (d, 1H, J=8.12 Hz); 5.48 (m, 2H); 4.18 (m, 1H); 3.41 (s, 8H); 3.12 (q, 1H); 2.86 (q, 1H); 2.80-2.57 (m, 8H); 2.36 (t, 2H, J=7.76 Hz); 2.25 (t, 2H, J=6.89 Hz); 1.63 (m, 2H); 1.54 (m, 2H); 1.43 (s, 36H); 1.33-1.23 (br, 32H); 0.86 (t, 6H, J=6.41 Hz). $^{13}$C-NMR (100 MHz, CDCl$_3$): 172.61, 172.25, 170.88, 163.22, 150.66, 140.94, 103.31, 86.38, 81.80, 72.04, 71.64, 56.06, 53.00, 51.21, 34.19, 33.98, 32.11, 29.87, 29.83, 29.73, 29.69, 29.55, 29.47, 29.44, 29.28, 28.36, 25.11, 24.86, 22.88, 14.32 ppm. FAB-MS m/z (M+1) calcd. 1149.78, found 1150.71.

Compound N4d: yield 950 mg (78.77%), colorless oil. $^1$H-NMR (400 MHz, CDCl$_3$): δ 10.01 (s, 1H); 7.76 (d, 1H, J=8.16 Hz); 6.14 (d, 1H, J=6.6 Hz); 5.78 (d, 1H, J=8.81 Hz); 5.52 (q, 1H); 5.47 (q, 1H); 4.17 (m, 1H); 3.42 (s, 8H); 3.14 (q, 1H); 2.87 (q, 1H); 2.78-2.58 (m, 8H) 2.35 (t, 2H, J=7.41 Hz); 2.23 (t, 2H, J=6.44 Hz); 1.62 (m, 2H); 1.54 (m, 2H); 1.42 (s, 36H); 1.30-1.18 (br, 40H); 0.86 (t, 6H, J=6.41 Hz). $^{13}$C-NMR (100 MHz, CDCl$_3$): 172.17, 172.07, 170.75, 163.70, 150.99, 140.80, 103.32, 86.01, 80.90, 71.66, 71.59, 55.94, 54.09, 52.86, 51.03, 34.09, 33.87, 32.02, 29.79, 28.26, 25.01, 24.76, 22.78, 14.24 ppm. FAB-MS m/z (M+1) calcd. 1206.84, found 1206.90.

Synthesis Example 4

Synthesis of the Ligands (Formula 2) and the Gadolinium complexes (Formula 1)

Trifluoroacetic acid (1.0 mL) was added to a solution of each of the compounds N4a-d in dry dichloromethane (5.0 mL) at 0° C. and then stirred at room temperature for another 12 h. The reaction mixture was concentrated and co-evaporated with diethyl ether. The residue was triturated with diethyl ether. The solid was filtered and recrystallized from ethanol/chloroform (4:1) to obtain the ligands L0-4.

Each of the ligands L0-4 (90 μM) was added to ultrapure water and the solution was adjusted to ~pH 7 with sodium bicarbonate. Gadolinium chloride hexahydrate (81 μM) was dissolved in 3.0 mL of ultrapure water and added to the solution of the ligand in three separate aliquots. After the addition of each aliquot, the pH was adjusted back to a pH between 6.5-7.0 using 0.1 M potassium carbonate solutions. The solution was allowed to stir for 30 min to allow for $Gd^{3+}$ chelation to occur, dialyzed against ultrapure water for overnight, and lyophilized to yield respective complexes.

Synthesis of Ligand L0 and Gadolinium Complex LGd1

Trifluoroacetic acid (1.0 mL) was added to a solution of the compound N3 (400 mg, 0.50 mmol) in dry dichloromethane (5.0 mL) at 0° C. and then stirred at room temperature for another 12 h. The reaction mixture was concentrated and co-evaporated with diethyl ether. The residue was triturated with diethyl ether. The solid product was filtered and re-dissolved in distilled water. Drying of the aqueous solution afforded 270 mg (94.73%) of ligand L0 as a colorless solid.

$^1$H-NMR (400 MHz, $D_2O$): δ 7.41 (d, 1H, J=8.12 Hz); 5.65 (d, 1H, J=8.04 Hz); 5.49 (d, 1H, J=3.56 Hz); 4.23 (q, 1H); 3.69 (s, 8H); 3.24 (br, 8H); 3.17 (m, 2H). $^{13}$C-NMR (100 MHz, $D_2O$): 171.57, 166.24, 151.33, 143.31, 102.40, 93.01, 78.92, 72.11, 71.27, 55.60, 55.48, 50.79, 50.64 ppm. ESI-MS m/z (M+1) calcd. 562.50, found 562.1. $Gd^{3+}$ complex ($C_{21}H_{27}GdN_5O_{13}^{-1}$): yield 90%: ESI-MS: m/z (M$^-$) ($C_{21}H_{27}GdN_5O_{13}$)$^-$ calcd. 715.09, found 715.00.

Synthesis of Ligand L1 and Gadolinium Complex LGd2

Trifluoroacetic acid (1.0 mL) was added to a solution of the compound N4a (520 mg, 0.50 mmol) in dry dichloromethane (5.0 mL) at 0° C. and then stirred at room temperature for another 12 h. Volatile components were removed from the reaction mixture in vacuo, and the residue was triturated with diethyl ether. The solid product was washed with dichloromethane and recrystallized from ethanol/chloroform to afford 320 mg (78.62%) of L1 as a colorless solid.

$^1$H-NMR (400 MHz, DMSO-$d_6$): 11.45 (s, 1H); 7.78 (d, 1H, J=8.04 Hz); 5.84 (d, 1H, J=5.67 Hz); 5.67 (d, 1H, J=8.01 Hz); 5.42 (dt, 1H); 5.17 (dt, 1H,); 4.39 (m, 1H); 3.41 (br, 9H); 2.94 (br, 9H); 2.33 (m, 4H); 1.50 (m, 4H); 1.22 (br, 16H); 0.84 (t, 6H, J=6.35 Hz). $^{13}$C-NMR (100 MHz, DMSO-$d_6$): δ 173.15, 172.94, 172.83, 164.77, 150.70, 102.22, 92.35, 81.94, 77.88, 71.68, 55.13, 52.23, 49.87, 33.47, 31.74, 29.08, 29.04, 29.00, 27.28, 24.72, 24.70, 22.54, 13.30 ppm. FAB-MS m/z (M$^+$) calcd. 813.4, found 813.6. $Gd^{3+}$ complex (LGd2) (yield 87%: ESI-MS: m/z 967.30 (M$^-$) ($C_{37}H_{55}GdN_5O_{15}$)$^-$ calcd. 967.30, found 967.40

Synthesis of Ligand L2 and Gadolinium Complex LGd3

Ligand L2 and gadolinium complex LGd3 were prepared in the same manner as in the synthesis of ligand L1 and complex LGd2, respectively. The yield was 76.2%.

$^1$H-NMR (400 MHz, MeOH-$d_4$): δ 7.64 (d, 1H, J=8.04 Hz); 5.77 (d, 1H, J=4.28 Hz); 5.71 (d, 1H, J=8 Hz) 5.32 (dt, 1H, J=5.56 Hz); 4.61 (t, 1H, J=7.16 Hz); 3.86 (m, 1H); 3.76 (m, 4H); 3.62 (s, 8H); 3.42 (br, 4H); 3.17 (br, 4H); 2.38 (m, 4H); 1.60 (m, 4H); 1.28 (br, 24H); 0.88 (t, 6H, J=5.6 Hz). $^{13}$C-NMR (100 MHz, DMSO-$d_6$): 173.19, 172.92, 172.60, 164.76, 150.70, 143.44, 102.22, 92.36, 77.89, 71.88, 55.01, 52.29, 49.84, 33.46, 31.90, 29.39, 24.67, 22.55, 13.32 ppm. ESI-MS m/z (M+H) calcd. 870.46, found 870.40. $Gd^{3+}$ complex (LGd3): yield 85.20%; ESI-MS m/z (M) ($C_{41}H_{63}GdN_5O_{15}$)$^-$ calcd. 1023.36, found 1023.50

Synthesis of Ligand L3 and Gadolinium Complex LGd4

Ligand L3 and gadolinium complex LGd4 were prepared in the same manner as in the synthesis of ligand L1 and complex LGd2, respectively. The yield was 82.2%.

$^1$H-NMR (400 MHz, DMSO-d6): ε 1.46 (s, 1H); 7.77 (d, 1H, J=10.46 Hz); 5.84 (d, 1H, J=4.96 Hz); 5.67 (d, 1H, J=7.88 Hz) 5.42 (t, 1H, J=5.52 Hz); 5.18 (t, 1H, J=5.36 Hz); 4.40 (m, 1H); 3.41 (br, 10H); 3.03 (br, 4H); 2.81 (br, 4H); 2.34 (m, 4H); 1.44 (m, 4H); 1.18 (m, 32H); 0.80 (t, 6H, J=6.32 Hz). $^{13}$C-NMR (100 MHz, DMSO-$d_6$): 173.53, 172.55, 172.41, 163.77, 150.96, 142.42, 103.10, 88.89, 81.16, 77.70, 71.70, 55.58, 55.43, 52.09. 50.07, 33.78, 32.78, 29.70, 29.67, 29.47, 29.24, 29.10, 28.39, 24.98, 22.81, 14.58 ppm. FAB-MS m/z (M) calcd. 926.53, found 926.00. $Gd^{3+}$ complex (LGd4): yield 89.5%: ESI-MS m/z (M+2) ($C_{45}H_{71}GdN_5O_{15}$+2H) calcd. 1081.43, found 1081.4.

Synthesis of Ligand L4 and Gadolinium Complex LGd5

Ligand L4 and gadolinium complex LGd5 were prepared in the same manner as in the synthesis of ligand L1 and complex LGd2, respectively. The yield was 82.2%.

$^1$H-NMR (400 MHz, DMSO-d6): δ 11.34 (s, 1H); 7.77 (d, 1H, J=8.04 Hz); 5.89 (d, 1H, J=5.28 Hz); 5.70 (d, 1H, J=8 Hz); 5.50 (t, 1H, J=5.81 Hz); 5.24 (t, 1H, J=5.48 Hz); 4.36 (m, 1H); 3.45 (s, 8H); 3.32 (m, 2H); 2.99 (br, 4H); 2.91 (br, 4H); 2.37 (t, 2H, J=4.2 Hz); 2.30 (t, 2H, J=5.21 Hz); 1.56 (br, 4H); 1.26 (br, 40H); 0.87 (t, 6H, J=641 Hz). $^{13}$C-NMR (100 MHz, DMSO-$d_6$): 173.51, 172.53, 172.39, 163.67, 150.98, 142.38, 103.11, 88.77, 77.83, 77.57, 55.50, 52.10, 50.14, 33.80, 32.02, 30.83, 20.79, 29.47, 29.21, 29.11, 28.40, 14.58 ppm. FAB-MS m/z (M+H) calcd. 982.59, found 982.80. $Gd^{3+}$ complex ($C_{49}H_{80}GdN_5O_{15}$): yield 87.22%: ESI-m/z (M$^-$) ($C_{49}H_{80}GdN_5O_{15}$)$^-$ calcd. 1135.48, found 1134.7.

Experimental Example 1

Relaxivity Measurements

Longitudinal and transverse relaxivities, $r_1$ and $r_2$, were measured at 20 MHz (0.47 T) and 60 MHz (1.41 T) at 36° C. on NMR (mq20 and mq60, Bruker, Germany) and animal MRI (Biospec 47/40, Bruker, Germany) systems. $T_1$ and $T_2$ relaxation times were measured with inversion recovery and spin-echo pulse sequences, respectively. The critical micelle concentration (cmc) of the complex LGd3 was determined by measuring the proton relaxation rate $1/T_1$ as a function of complex LGd3 concentration.

The relaxation efficiency of the newly synthesized amphiphilic MRI contrast agents according to the present invention was determined by measuring longitudinal relaxivity ($r_1$) and transverse relaxivity ($r_2$) at 20 MHZ (0.47 T) and 60 MHz (1.41 T) in phosphate buffered saline (PBS) solution at 36° C. The results are shown in Table 1. Relaxivities ($r_1$ and $r_2$) (in units of $mM^{-1}s^{-1}$ per mM of MR contrast agents in PBS solution without and with 0.65 mM HSA at 0.47 T and 1.41 T, 36° C.

TABLE 1

| Compound | Relaxivity | | | | | | |
|---|---|---|---|---|---|---|---|
| | 20 MHz (0.47 T) | | | | 60 MHz (1.41 T) | | |
| | $r_1$ | $r_2$ | $r_2/r_1$ | $r_1{}^a$ | $r_1$ | $r_2$ | $r_2/r_1$ |
| LGd1 | 5.10 | 7.20 | 1.41 | 5.62 | 4.17 | 21.50 | 5.15 |
| LGd2 | 14.70 | 15.90 | 1.08 | 31.90 | 12.40 | 32.40 | 2.61 |
| LGd3 | 30.30 | 31.30 | 1.03 | 41.00 | 23.40 | 55.90 | 2.47 |
| LGd4 | 27.10 | 26.20 | 0.96 | 38.50 | 16.50 | 47.20 | 2.86 |
| LGd5 | 20.10 | 28.71 | 1.40 | 26.40 | 17.20 | 49.80 | 2.89 |
| Magnevist® | 4.70 | 5.60 | 1.19 | —b | 3.81 | 18.80 | 4.93 |
| Omniscan® | 4.41 | 5.60 | 1.26 | —b | 3.68 | 19.60 | 5.32 |

In the case of the amphiphilic complexes LGd2-5 according to the present invention, relaxivity was increased 3-6 fold compared to Magnevist® and Omniscan®, depending on variable chain length and particle size (FIGS. 6 to 9).

The relaxivity value ($r_1$) for LGd3 reached a maximum of 30.3 and 23.4 mM$^{-1}$s$^{-1}$ at 0.47 T and 1.41 T, respectively, indicating 6-fold higher than Gd-DTPA and Gd-DTPA-BMA. The ability of the corresponding amphiphilic conjugates for supramolecular self-assembly can slow molecular tumbling of the complex and global rotational motion, enhancing the $r_1$ of each complex. To the best of our knowledge, the relaxivity ($r_1$) of LGd3 is the highest value at 60 MHz (1.41T) in PBS solution among the reported amphiphilic series.

From the DLS data as shown in FIGS. 6 to 9, the average particle size of LGd3 was the largest (51.16 nm), which significantly reduces rotational motion as a cause of increased relaxivity ($r_1$) compared to others. The $r_2/r_1$ ratio of the amphiphilic complexes LGd2-5 according to the present invention was reduced, especially at a high magnetic field (60 MHz) (1.41 T) compared to Gd-DTPA and Gd-DTPA-BMA. This clearly indicates that the new contrast agents of the present invention would be better $T_1$ contrast agents at a higher magnetic field.

Experimental Example 2

Measurements of MR Phantom Images

To directly visualize the enhanced relaxivity of LGd1-4 and the potential for increasing resolution, a MR phantom was imaged using a 63.8 MHz (1.5 T) (Signa EXCITE, GE, USA) clinical MR scanner with increasing molecular concentration of the complexes (FIG. 1).

FIG. 1 shows a $T_1$-weighted spin-echo MR image (FOV=7 cm; matrix=256×256; TE/TR=11/100 ms; slice thickness=2 mm; number of acquisitions=50) for the complexes LGd1-4 and Mag (Magnevist®, Gd-DTPA) in PBS solution at six different concentrations (1.0, 0.75, 0.5, 0.25, 0.125, and 0 mM) of the complexes at 63.8 MHz (1.5 T) and 36° C.

The image clearly reveals that LGd1-4 of the present invention provide brighter contrast than Gd-DTPA, even in the presence of lower concentrations of gadolinium ions (Gd$^{3+}$). The brightness, especially in Gd$^{3+}$ concentrations below 0.5 mM, is well in accordance with the $r_1$ relaxivity value at 60 MHz, LGd3>LGd4>LGd2>LGd1.

Experimental Example 3

Interaction with Human Serum Albumin (HSA)

It is well known that non-covalent interaction of the contrast agent with human serum albumin (HSA) increases its circulation time in blood and slows down tubling rate, leading to greater contrast enhancement for blood vessel imaging. In this example, effective interaction between the newly synthesized contrast agents (CAs) and human serum albumin (HSA) were investigated.

Human serum albumin (HSA; Product No. A3782) was purchased from Sigma (Bornem, Belgium) and was used without further purification. HSA binding experiment was performed with 50 µM of the complexes LGd1-5 in PBS solution depending on the concentration of HSA from 0 to 4 mM at 20 MHz and 36° C.

Figure 2:
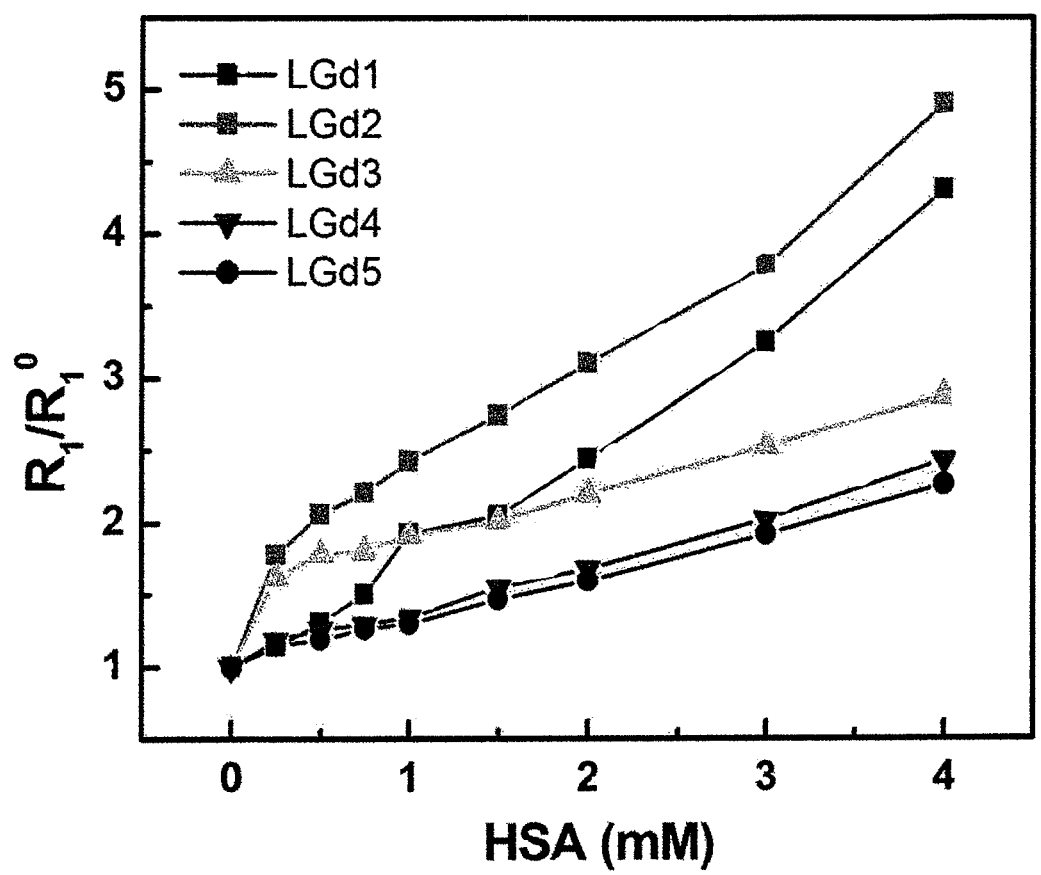
FIG. 2 shows changes in the $^1$H relaxation rate of 50 μM solutions of complexes depending on the concentration of human serum albumin (HSA) at 20 MHz (0.47 T) and 36° C.

FIG. 2 shows changes in the $^1$H relaxation rate of 50 µM solutions of the complexes depending on the concentration of human serum albumin (HSA) at 20 MHz (0.47 T) and 36° C. This graph shows that the $R_1/R_1{}^0$ values ($R_1$=relaxivity in the presence of HSA, $R_1{}^0$=relaxivity in the absence of HSA) increased gradually with increasing HSA concentration at a particular concentration (50 µM) of the contrast agent. In addition, it is clearly shown in serum albumin (HSA) concentration below 1.0 mM that effective interaction of the amphiphilic complexes LGd2 and LGd3 with human serum albumin (HSA) is high comparable to LGd1 and other amphiphilic complexes, LGd4 and LGd5. The increment of $R_1/R_1{}^0$ with increasing aliphatic chain length is: LGd2>LGd3>LGd4>LGd5.

The highest relaxivity (41.0 mM$^{-1}$s$^{-1}$) (Table 1) at 20 MHz (0.47 T) in PBS solution at a human physiological concentration of human serum albumin (HSA) (0.65 mM) was obtained in the case of LGd3. This value is same with the clinically applied angiographic phosphodiester-Gd-DTPA (Vasovist®, Bayer Schering, Germany) under identical conditions.

Figure 10:
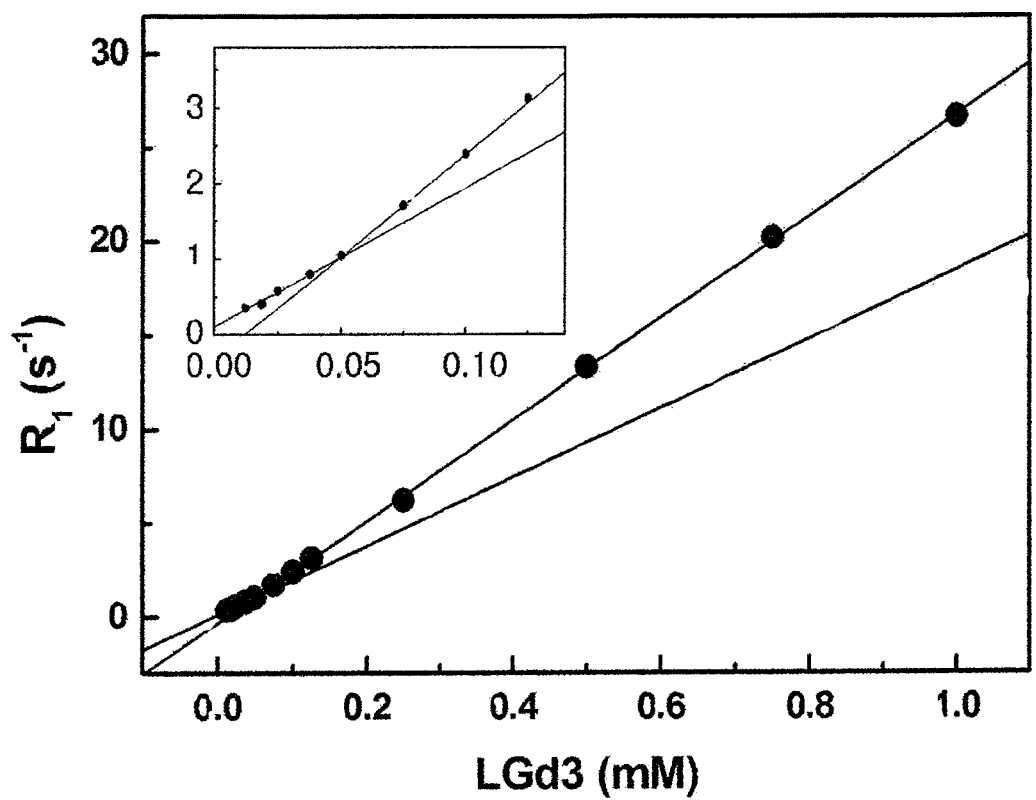
FIG. 10 shows the critical micelle concentration (CMC) of LGd3 micelles at 20 MHz and 36° C. The inset shows that the CMC value was about 0.05 mM.

Furthermore, to know the non-covalent binding strength between HSA and the complex, a binding constant ($K_a$) of (3.34±0.28)×10$^3$ M$^{-1}$ for the complex LGd3 was determined using the theoretical equation reported in the reference (D. T. Schuhle, J. Schatz, S. Laurent, L. V. Elst, R. N. Muller, M. C. A. Stuart, J. A. Peters, Chem. Eur. J. 2009, 15, 3290). The relaxivity for the non-aggregate form of LGd3 ($r_1{}^f$) was measured to be 18.5 mM$^{-1}$s$^{-1}$ (below CMC=50 µM; FIG. 10), while for adduct LGd3.HSA ($r_1{}^c$), 41.0 mM$^{-1}$s$^{-1}$ at 36° C. and 20 MHz (0.47 T) in PBS solution. This binding constant is significantly higher compared to recently reported calyx [4]arene-DOTA conjugated amphiphile, indicating that the nucleoside has considerable binding affinity with human serum albumin (HSA) as speculated above. As a result, the complex LGd3 of the present invention could be retained in vivo for a longer time.

Experimental Example 4

Measurements of pH Dependence of Relaxivity

There has recently been an increasing demand for pH-responsive contrast agents. Particularly, in in vivo pH mapping of tissues, pH-responsive contrast agents are very important in the diagnosis of cancers such as melanoma whose extracellular pH (pH$_e$) is lower by almost 0.6 than that of healthy subcutaneous tissue.

The relaxivities of the non-aggregated complex LGd1 and the most aggregated complex LGd3 (FIG. 7, average diameter 51.16 mm) were investigated at various pH values (3.5-11) at 60 MHz (1.41 T) and 36° C.

Figure 11:
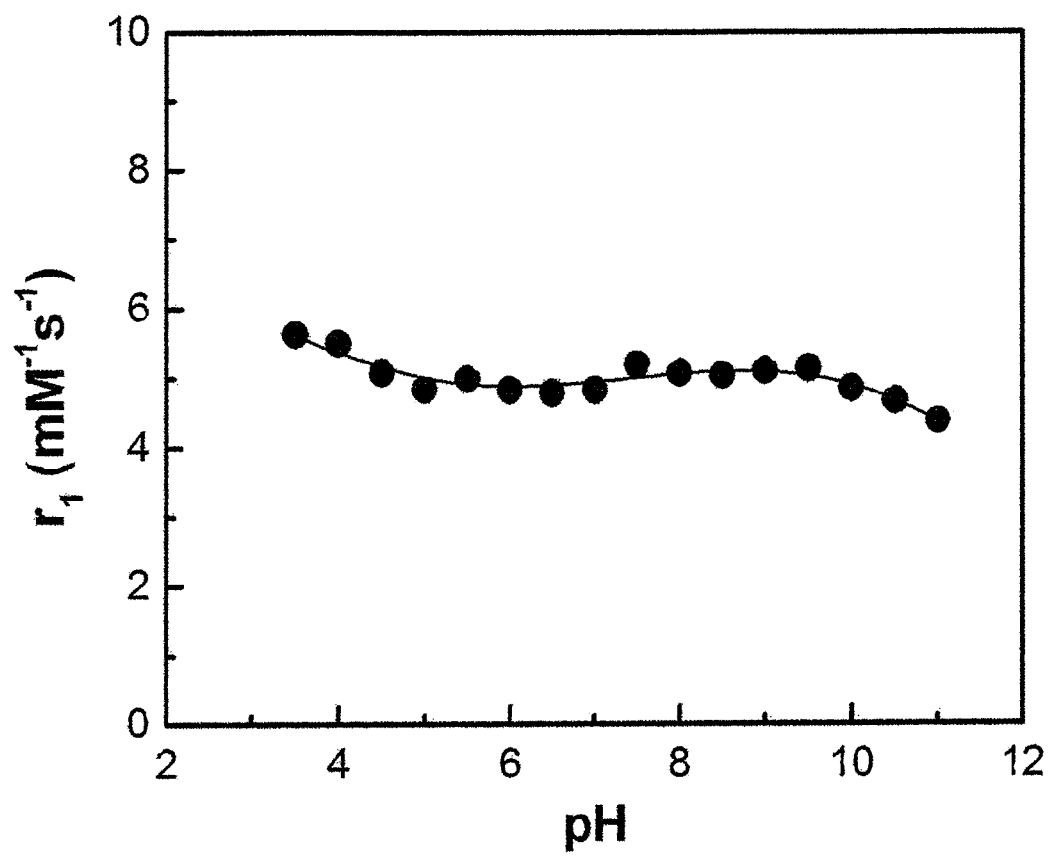
FIG. 11 shows the pH dependence of water $^1$H relaxivity for the complex LGd1 at 60 MHz (1.41 T) and 36° C. The relaxivity was 5.0±0.6 mM$^{-1}$s$^{-1}$ in the given pH range.

Interestingly, no precipitation was observed in such broad pH range. The relaxivity of the complex LGd3 increased gradually with increasing pH (up to a maximum of 8) (FIG. 3), and thereafter decreased sharply at a pH between 8.0 and 9.5. The relaxivity of the complex LGd1 was in the range of 5.0±0.1 mM$^{-1}$s$^{-1}$ and decreased by about 10% at an alkaline pH of 11 (FIG. 11).

Figure 3:
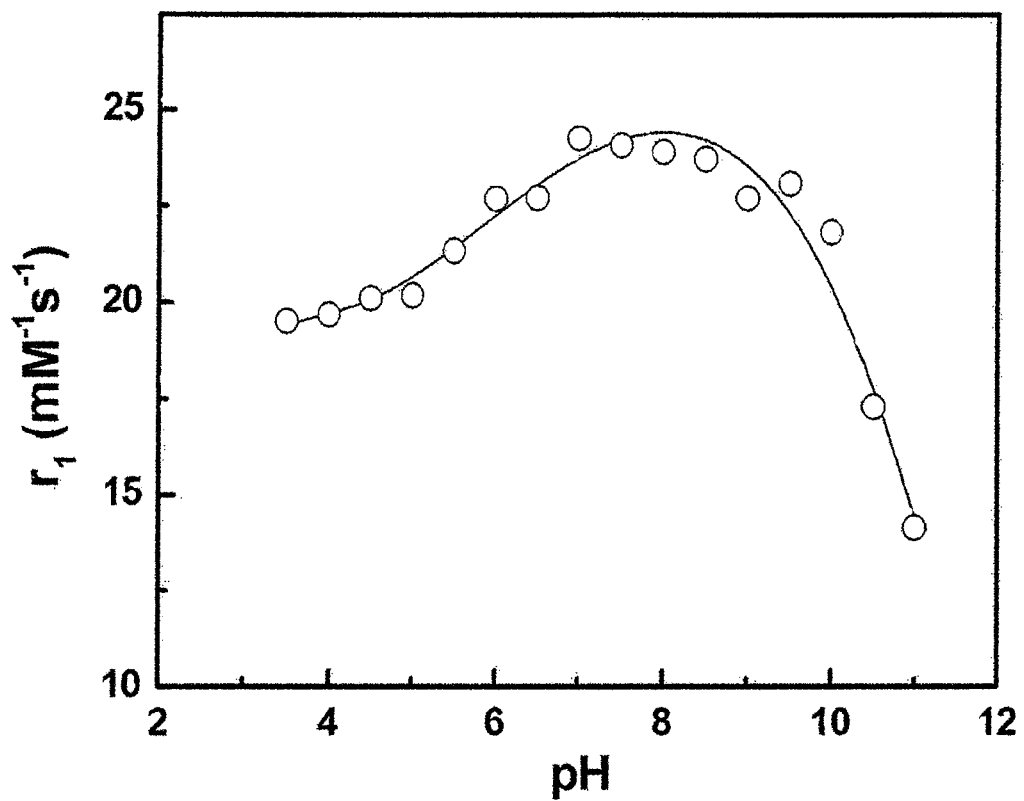
FIG. 3 shows the pH dependence of water $^1$H-NMR relaxivity for the complex LGd3 at 60 MHz (1.41 T) and 36° C.

Specifically, the relaxivity of LGd3 was about 24.5 mM$^{-1}$s$^{-1}$ at pH 8 and decreased gradually to 14.2 mM$^{-1}$s$^{-1}$ at pH 11 (approx. $\Delta r_1$=10.3). This relaxivity was recovered depending on pH. At a pH between 6 and 7.5, which is the most important range, the relaxivity variation $\Delta r_1$ was ~2.9 (FIG. 3). These observations suggest that the complex LGd3 has the ability to distinguish normal tissues (pH 7.3-7.6) and cancers (pH 6.6-6.9).

FIG. 3 shows the pH dependence of water $^1$H-NMR relaxivity for the complex LGd3 at 60 MHz (1.41 T) and 36° C. The pH dependence of water $^1$H-NMR relaxivity $r_1$ was obtained at 60 MHz and 36° C. The complexes LGd1 and LGd3 were dissolved in previously prepared stock solutions (StockOptions pH Screen, Hampton Research, USA) at pH 3.5-11.

pH-dependent relaxivity variation can be explained based on proton exchange rate or molecular rotation rate. Low relaxivity of an anionic complex at a low pH is due to the protonation of the anionic complex. The anionic complex is present in a large amount with increasing pH, resulting in an increase in proton exchange rate. The relaxivity of the anionic complex reaches the highest value at pH 8. The intramolecular hydrogen bonds are hindered at pH≥8, which is believed to cause collapse of self-assembled aggregates.

Figure 12:
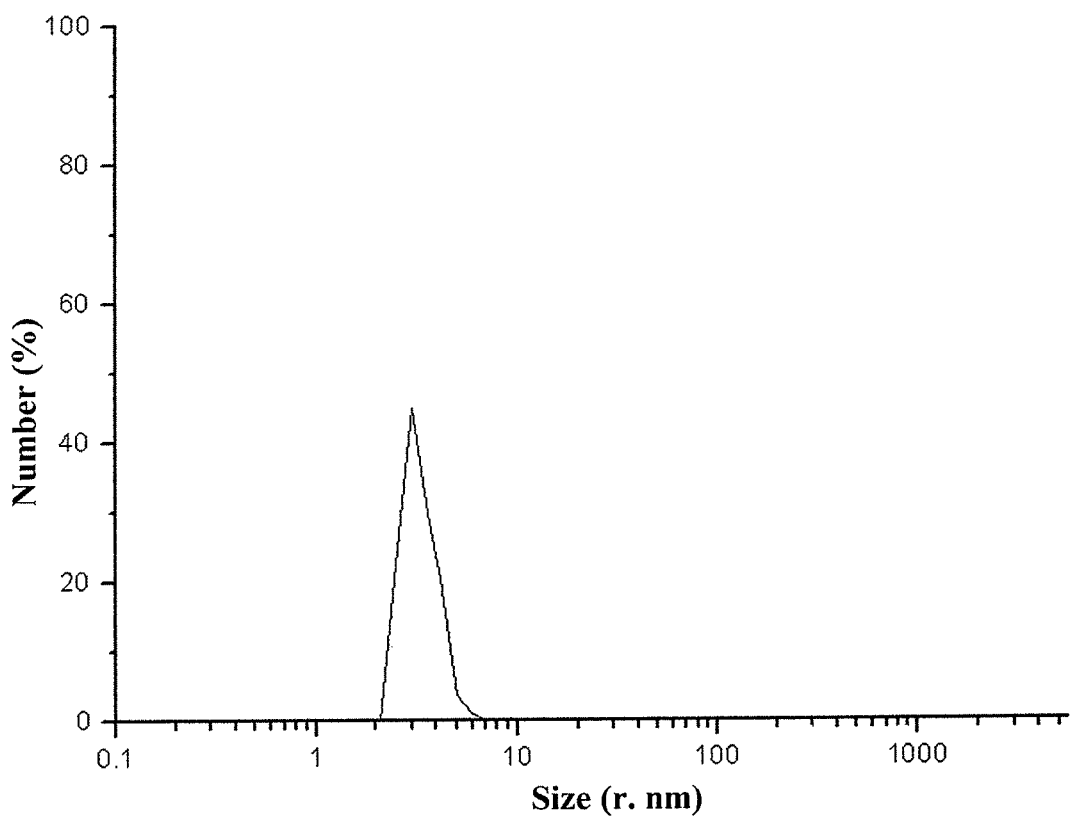
FIG. 12 shows the results of DLS for LGd3 micelles (average size 1.02 nm, PDI 2.01).

DLS studies indicated that the average diameter of LGd3 was drastically changed from 51.15 to 1.2 nm with varying pH from 7.4 to 10.5 (FIG. 12). The rotational motion was increased with decreasing particle size, and as a result, a relaxivity as low as about 17.3 mM$^{-1}$s$^{-1}$ was obtained at a pH of 10.5.

Experimental Example 5

Stability of Gadolinium Complexes

The stability of the gadolinium complex against various biologically active metal ions is very important in in vivo applications. Among them, only Zn$^{2+}$ can displace significant amounts of the Gd$^{3+}$ ion as concentration of Zn$^{2+}$ in blood is relatively high (55-125 μM/L). The stability of the complexes LGd1-4 against transmetallation by Zn$^{2+}$ was studied employing the method of others.

Figure 13:
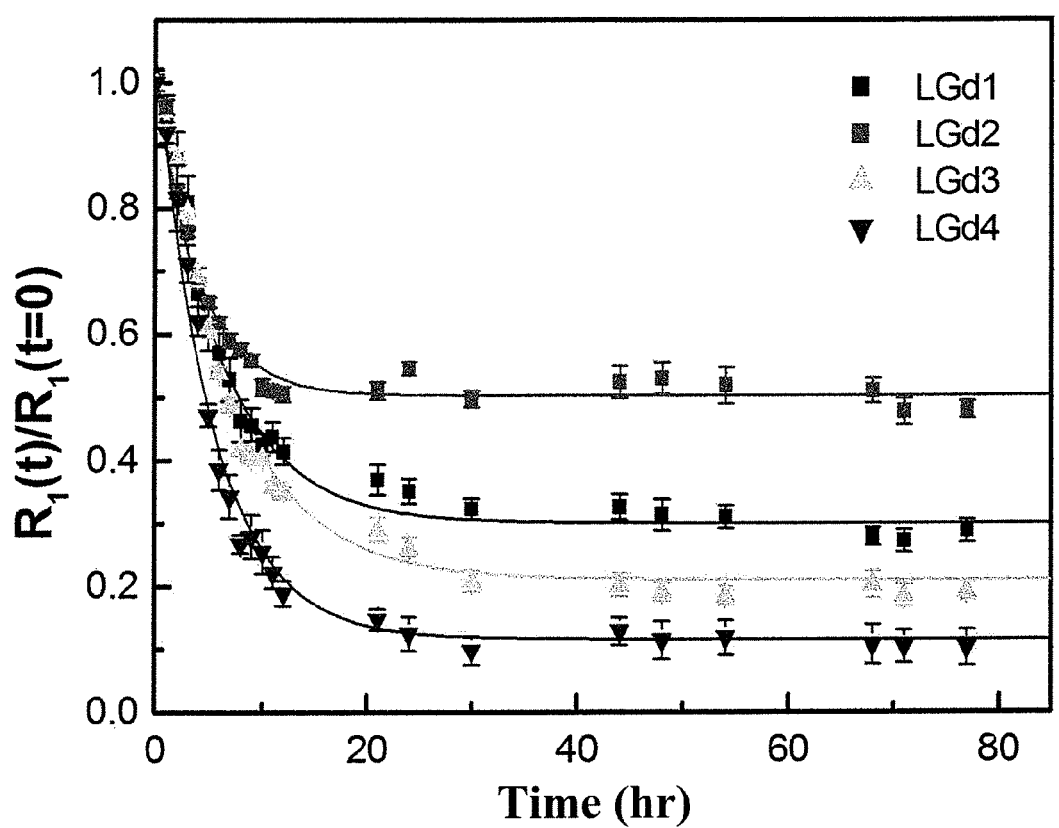
FIG. 13 shows time evolution of proton relaxation rate during transmetallation of the complexes by Zn (II) ions in PBS solution at 20 MHz (0.47 T) and 36° C. The solid lines are fitted ones by a function of y$_0$+A×exp(–t/C$_1$), and the y$_0$ values (at steady state in about 70 h) were 0.30, 0.50, 0.21, and 0.12 for the compounds LGd1, LGd2, LGd3, and LGd4, respectively.

The time evolution of the $^1$H longitudinal relaxivity (R$_1$) of a 2.5 mM gadolinium complex with 2.5 mM ZnCl$_2$ in PBS solution was measured. Stability of the amphiphilic complex LGd2 of the present invention was greater than that of the non-aggregated complex LGd1 (FIG. 13). After 70 h, the relaxivities were retained 30, 50, 21, and 12% for LGd1-4, respectively. The values were within those of the clinically used commercial MRI T$_1$ contrast agents (CAs), Gd-DTPA and Gd-DTPA-BMA, for which these are 50% and 10%, respectively.

Experimental Example 6

MRI Measurements

The stability studies of the complexes of the present invention against transmetallation indicated that the complexes are quite stable in in vitro experiments and are not degraded under physiological conditions. LGd3 as an example of nucleoside-based Gd$^{3+}$-chelated amphiphiles was evaluated for MR imaging in mice. Hydrophobic moieties generally tend to accumulate in the liver, which provides dual features of an extracellular contrast agent and a hepatocyte-specific agent. According to this property, diphenylcyclohexyl phosphodiester-Gd-DTPA (Vasovist®), Gd-BOPTA (Multihance®, Bracco, Italy), and Gd-EOB-DTPA (Primovist®, Schering AG, Germany) have been used clinically as as liver-specific contrast agents.

These contrast agents are partially excreted from the blood through the hepatobiliary systm with partial excretion through the kidneys (Vasovist®: 91% renal, 8% hepatic; Multihance®: 96% renal, 4% hepatic; Primovist®: 50% renal, 50% hepatic).

The whole-body pharmacokinetics of T$_1$ contrast agents can be measured by dynamic 2D or 3D MR imaging. Contrast-to-noise ratios (CNRs) in the liver and blood of MR images were measured to compare dynamic behaviors between the complex LGd3 of the present invention and clinically available contrast agent Gd-DTPA-BMA.

5-Week-old male Balb/C mice (n=3; OrientBio, Korea) were used for contrast-enhanced dynamic MRI. MRI was performed by using a 4.7 T MRI system (BioSpec 47/40; Bruker, Germany) with a quadrature birdcage RF coil (35 mm inner diameter) for signal transmission and reception.

Before and after injection of the contrast agents LGd3 and Gd-DTPA-BMA, dynamic T$_1$-weighted MR imaging was carried out. Bolus of the contrast agents (0.1 mmol Gd/kg) was injected via tail vein. During MRI acquisition, the animals were anesthetized using 1-1.25% of inhalational isoflurane with O$_2$:N$_2$O (3:7) mixture.

To quantitatively measure signal intensity in region-of-interests (ROIs) as contrast-noise ratio (CNR), a reference of water sample (1 g/l CuSO$_4$ in 8:2 of D$_2$O:H$_2$O) in a cylindrical tube (5 mm diameter) was used.

Dynamic 2D T$_1$-weighted images were acquired using a spin-echo (SE) pulse sequence with the following parameters: TE/TR=10/400 ms, number of average=4, matrix size=256×256, slice thickness=1 mm, field of view=30×30 mm$^2$ (in axial slice) or 50×30 mm$^2$ (in coronal slice), and scan time=6 min 50 s).

Dynamic 3D T$_1$-weighted images were acquired using a fast low angle shot gradient echo (FLASH) pulse sequence with parameters of TE/TR=2.4/7.5 ms, number of average=4, flip angle=30°, field of view=30×30×20 mm$^3$, matrix size=256×256×128, and scan time=12 min 17 s.

Figure 4:
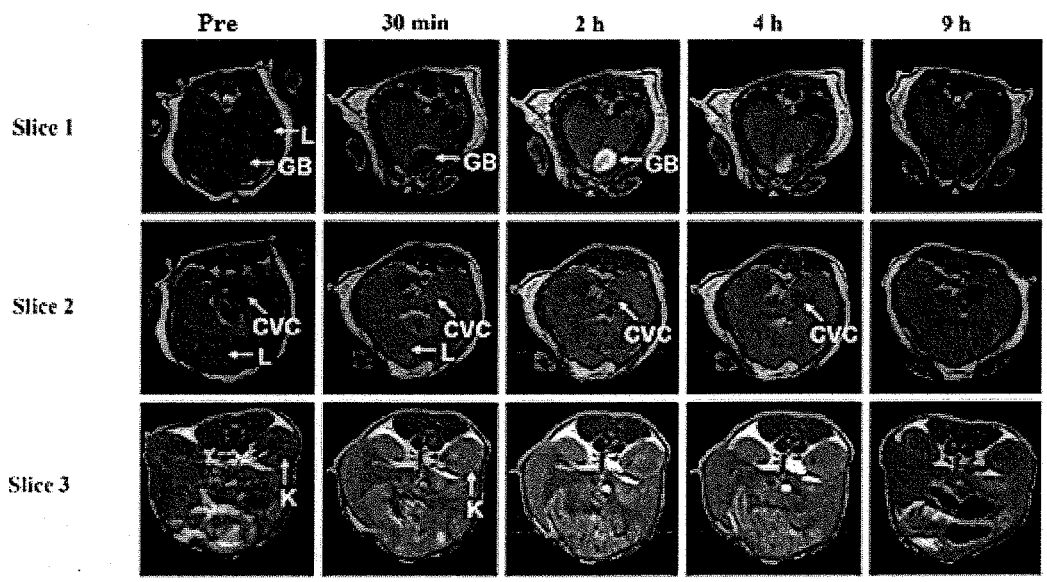
FIG. 4 shows sequential dynamic two-dimensional MR images of mice before and after intravenous injection with 0.1 mmol of Gd/kg of LGd3.

FIG. 4 shows sequential dynamic two-dimensional MR images of mice before and after intravenous injection with 0.1 mmol of Gd/kg of LGd3. A spin-echo (SE) pulse sequence was used with the following parameters: TE/TR=10/400 ms, number of average=4, matrix size=256×256, slice thickness=1 mm, and field of view=50×30 mm$^2$. On images obtained 30 min after injection of LGd3, T$_1$-contrasted enhancement in liver parenchyma (L), caudal vena cava (CVC), and kidney (K) was markedly seen, but there was no relative signal intensity (SI) change compared with pre-SI in gall bladder (GB). A bright contrast enhancement in GB was also noticed within 2-4 h after injection, while SI in CVC was almost recovered and low at 2 h after injection. At 9 h after injection, SI in liver was still relatively high compared with pre-injection value.

Example 7

Evaluation of Liver Specificity

Figure 5:
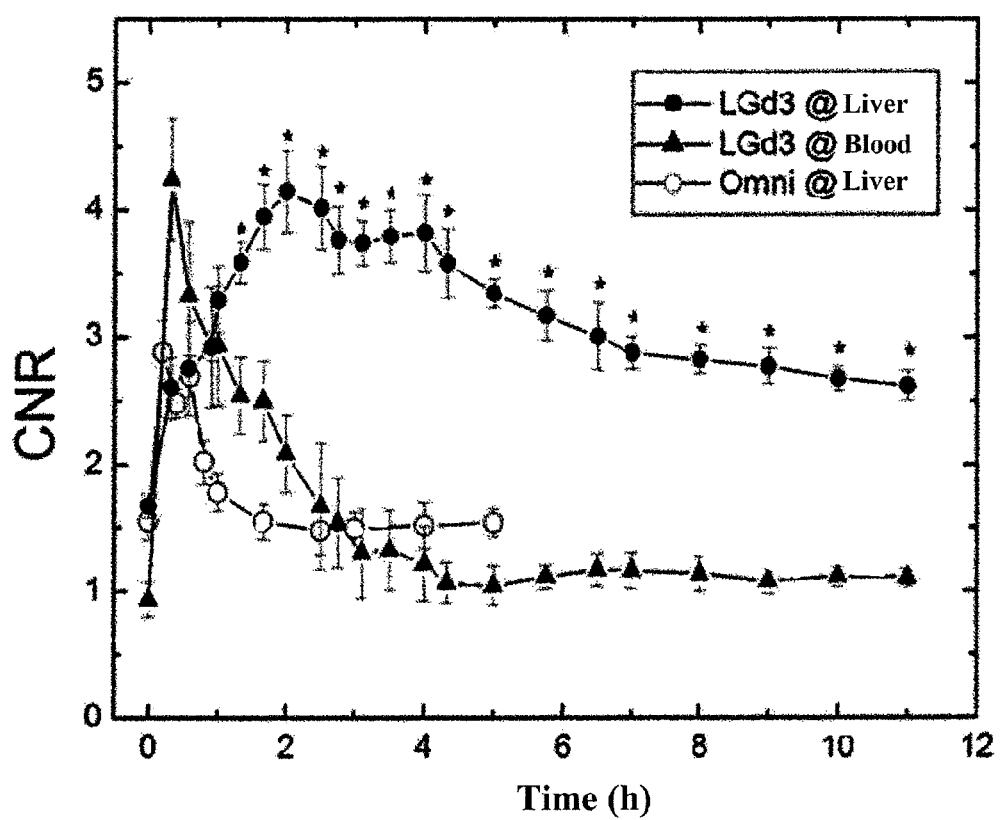
FIG. 5 is a graph showing time variations of contrast-to-noise ratio (CNR) in the mouse liver (●) and blood (caudal vena cava: (▲) obtained after injection of LGd3 with 0.1 mmol Gd/kg compared with the change in the mouse liver following injection of a commercial T$_1$ contrast agent Gd-DTPA-BMA (Omniscan®) with 1 mmol Gd/kg (○).
Figure 6:
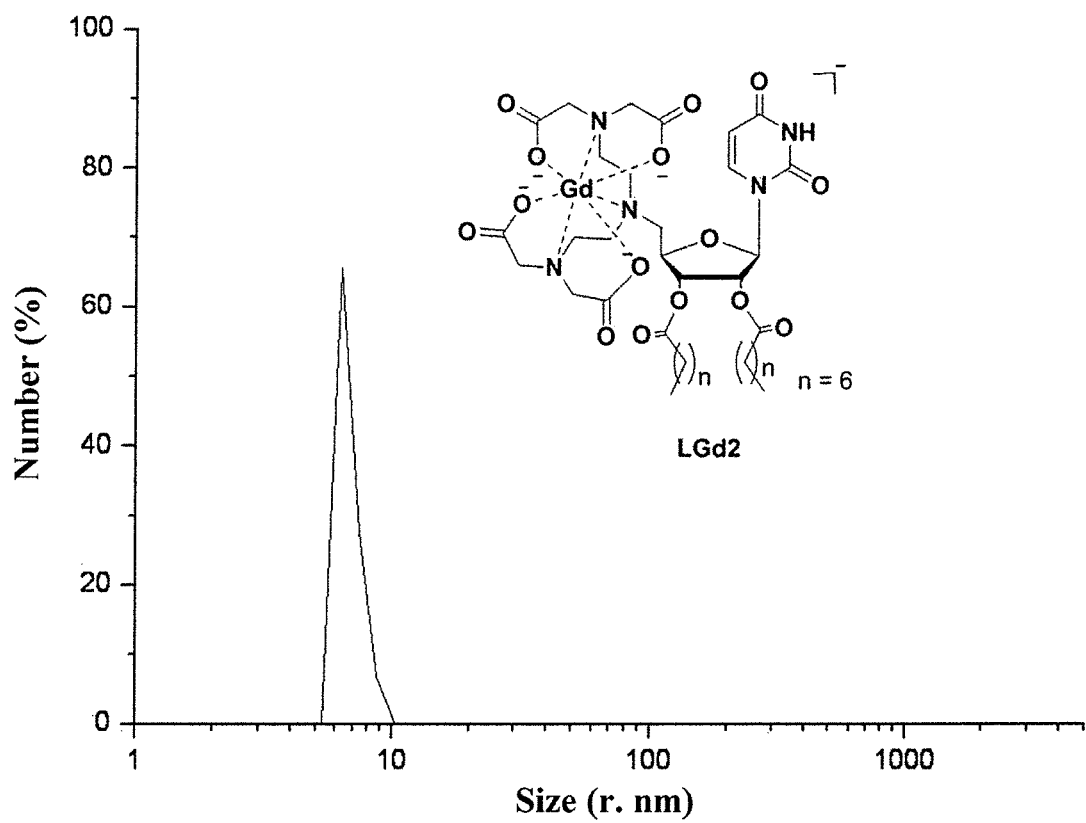
FIG. 6 shows the results of dynamic light scattering (DLS) for LGd2 micelles (average size 6.78 nm, PDI 0.986).
Figure 7:
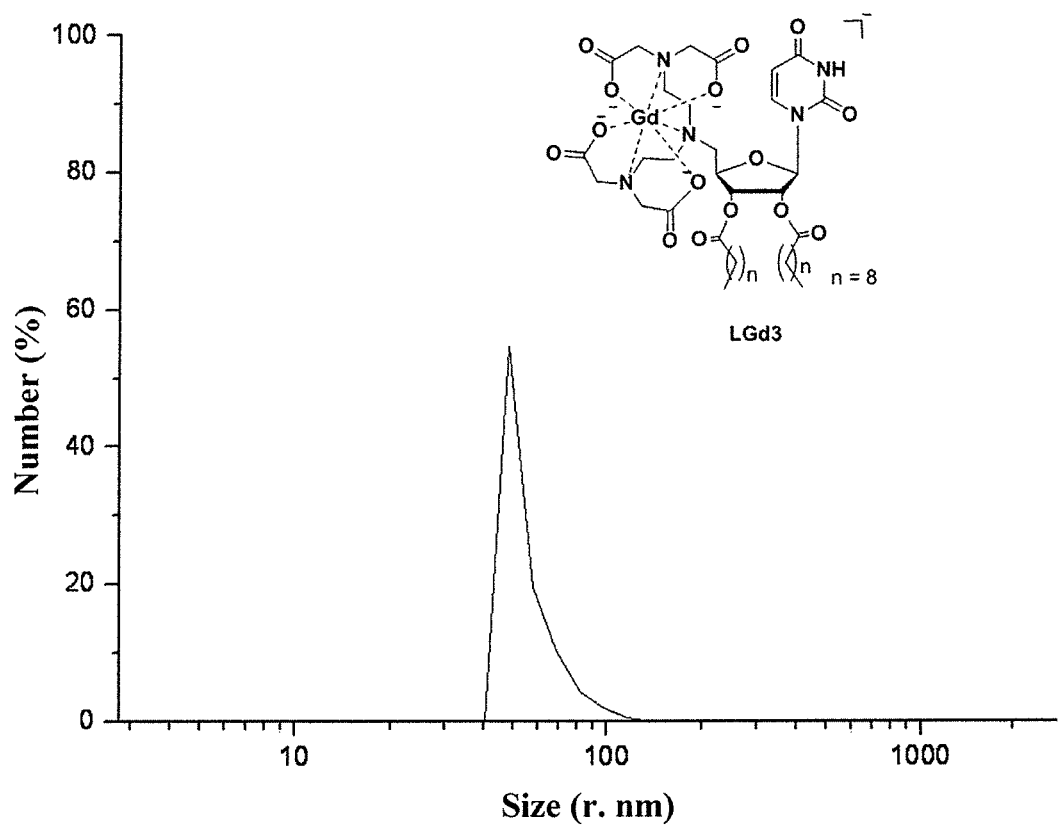
FIG. 7 shows the results of DLS for LGd3 micelles (average size 51.16 nm, PDI 1.46).
Figure 8:
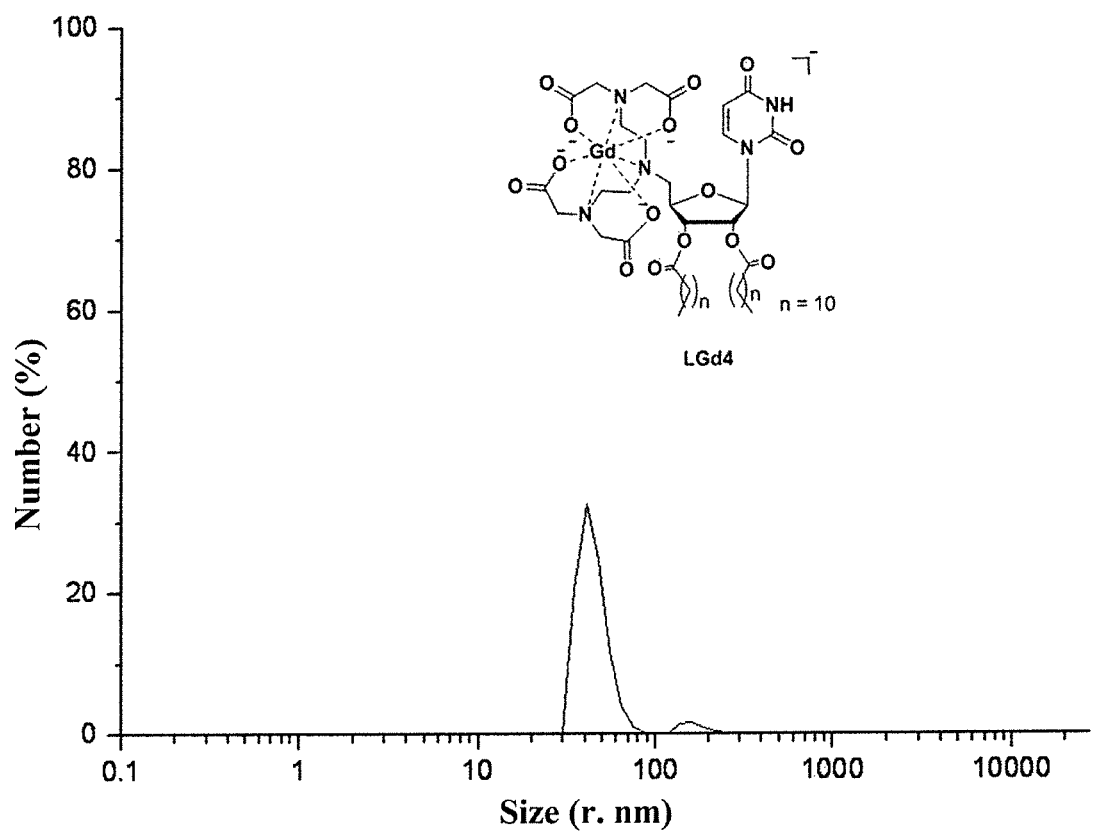
FIG. 8 shows the results of DLS for LGd4 micelles (average size 50.16 nm, PDI 1.12).
Figure 9:
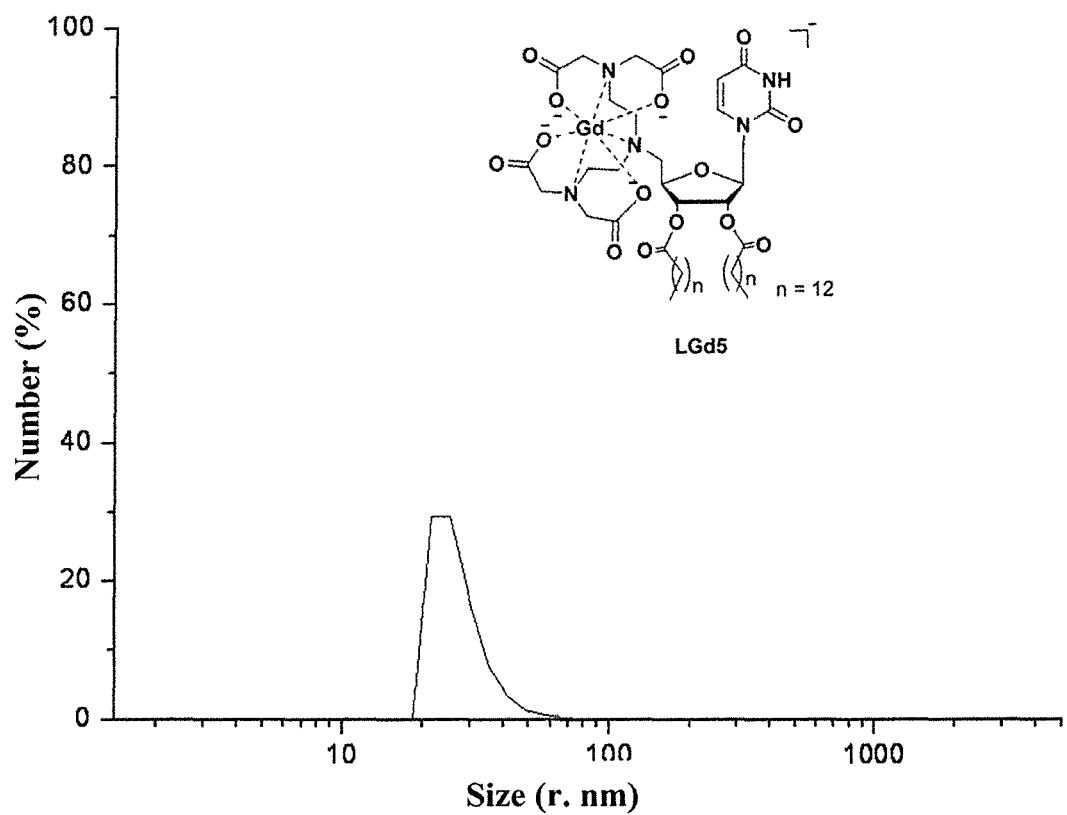
FIG. 9 shows the results of DLS for LGd5 micelles (average size 24.74 nm, PDI 1.14).

FIG. 5 is a graph showing time variations of contrast-to-noise ratio (CNR) in the mouse liver (●) and blood (caudal vena cava: ▲) obtained after injection of LGd3 with 0.1 mmol Gd/kg compared with the change in the mouse liver following injection of a commercial T$_1$ contrast agent Gd-DTPA-BMA (Omniscan®) with 1 mmol Gd/kg (○). The CNR value in the liver after injection of LGd3 was gradually increased and was almost maximum at 2-4 h after injection, then was decreased gradually with time for 11 h, at which it was still about 60% higher than the pre-value. After injection of LGd3 the CNR in blood was almost recovered to the initial value and showed a tendency similar to the case of Gd-DTPA-BMA except a relatively long retention time. Asterisks denote significant difference (P<0.01, liver vs. blood and pre-injection liver) in CNR.

Figure 14:
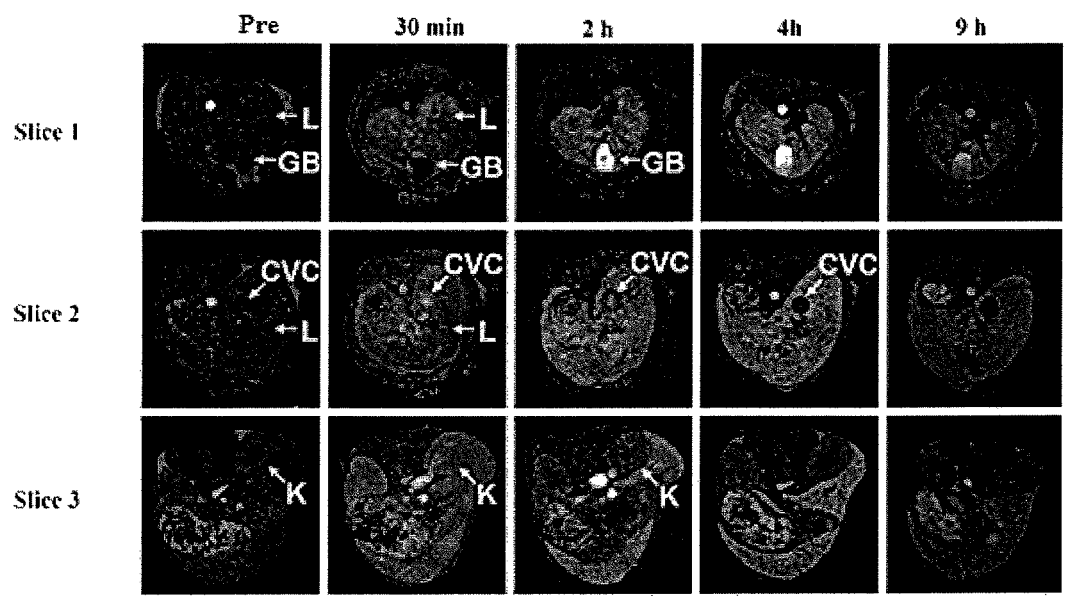
FIG. 14 shows dynamic 3D MR images in three representative axial planes of a mouse injected with 0.1 mmol of Gd/kg of LGd3 at several time points. T$_1$-weighted fast low angle shot gradient echo (FLASH) pulse sequence was used with the following parameters: TE/TR=2.4/7.5 ms, number of average=4, flip angle=30°, field of view=30×30×20 mm$^3$, matrix size=256×256×128, and scan time=12 min 17 s).

Quantitative analysis of the time-course CNR change of mice obtained from 3D dynamic images (FIG. 14) showed that injection of 0.1 mmol Gd/kg of LGd3 created more intense and prolonged enhancement in the liver parenchyma than injection of same dose of Gd-DTPA-BMA (FIG. 5). Peak and plateau enhancement in liver parenchyma was observed between 1.5 and 4 h after injection of the contrast agent LGd3, and it was about 240% (from 1.67 to 4.0 of CNR in liver). This signal enhancement was much higher compared to reported amphiphilic hydroxypyridonate-terephthalimide-based contrast agent, heterotripodal hydroxypyridonate-terephthalamide (HOPOTAM) with hydration number 2; where SI enhanced by 165% within 5 min of injection and then dropped quickly.

In the reported case of DTPA-based amphiphile, the enhancement was 102%. At this time point the liver enhancement was relatively comparable to that of commercial liver-specific CA, Gd-EOB-DTPA (Primovist®, Schering AG, Germany). Also the peak CNR value of Gd-DTPABMA was smaller than that with LGd3, and it was about 2.8, at times between 0.2 and 0.6 h, and then the CNR value was decreased faster than that of LGd3. It was observed that within 2 h after injection of LGd3, the CNR in blood was significantly high compared with pre-CNR, indicating that the perfusion phase lasts at this time point. Note that, about 3 h after injection of LGd3, the CNR in blood almost recovered to the initial value, which was attributable to the excretion of LGd3 from blood through kidney within 3 h. It implied therefore that signal intensity in liver after 3 h was entirely due to accumulation of LGd3 in hepatocytes.

The maximum liver enhancement was attained in the end of perfusion phase at about 2 h post-injection, and then plateau-like constant CNR with marked enhancement was maintained for about 2 h.

In the delayed hepatobiliary organ-specific phase, that CNR in the liver parenchyma was significantly higher than blood and the CNR in the blood was almost recovered to the pre-value. Hyperintense CNR in the liver during the delayed hepatobiliary phase could be obtained 2 h after injection of LGd3 and lasted for at least 11 h. The pharmacokinetic property of LGd3 was similar to commercially available hepatobiliary MR contrast agents, Gd-BOPTA, Gd-EOB-DTPA, and MS-325, in the viewpoint of excretion of contrast agents through biliary ducts and intestine. The property of biliary excretion of LGd3 would provide with high specific and sensitive detection of liver metastases, particularly smaller lesions.

In conclusion, uridine nucleoside-based amphiphilic gadolinium complexes were synthesized in the present invention. The highest relaxivities ($r_1$) achieved were 30.3 and 23.4 $mM^{-1}s^{-1}$ in phosphate buffered saline solution (pH 7.4) at 0.47 T and 1.41 T, respectively, for LGd3 as one of the complexes according to the present invention. The new complexes of the present invention demonstrated binding affinity towards human serum albumin with further enhanced relaxivity. The relaxivity of the amphiphilic contrast agent LGd3 was changed depending on the pH of solution. The stability studies of the complexes against transmetallization with $Zn^{2+}$ indicated that the new amphiphilic complexes of the present invention are quite stable and comparable with clinically used Gd-DTPA and Gd-DTPA-BMA. In vivo pharmacokinetics of the new complexes according to the present invention showed that the complexes are highly specific for hepatocytes causing excretion into bile ducts, gall bladder, and intestines, and therefore, they may be highly potential $T_1$ contrast agents to provide with detection of small lesions in liver.

INDUSTRIAL APPLICABILITY

The uridine-based gadolinium complex of the present invention is first example of a self-assembled paramagnetic amphiphile with high relaxivity, significant binding ability with human serum albumin, pH response, and high liver specificity. The contrast agent including the uridine-based gadolinium complex represents an important and highly efficient nanosystem in MRI applications.

The invention claimed is:

1. A method for preparing a uridine-based gadolinium complex of Formula 1, as depicted in Scheme 1-1:

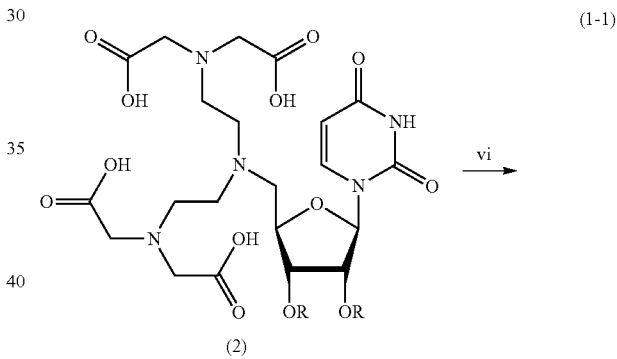

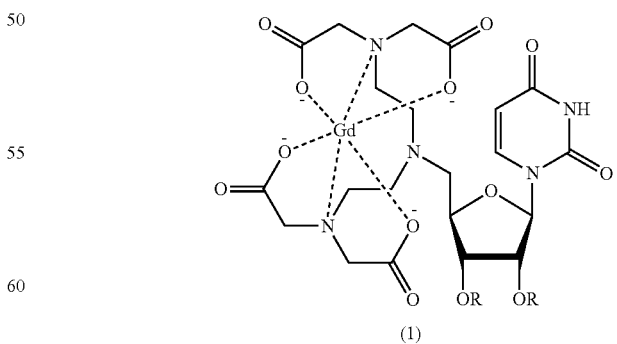

wherein vi represents $GdCl_3 \cdot 6H_2O$, $H_2O$, and $Na_2CO_3$.

2. A method for preparing a uridine-based gadolinium complex of Formula 1, as depicted in Scheme 1-2:

19

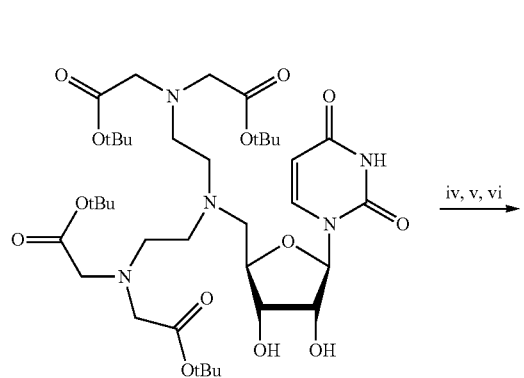
(1-2)

(N3)

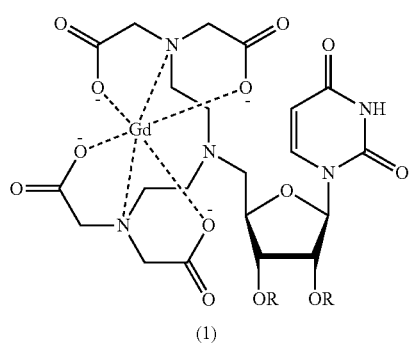
(1)

wherein iv represents $RCO_{2H}$; EDCI, DMAP, and DMF; v represents TFA and DCM; and vi represents $GdCl_3 \cdot 6H_2O$, $H_2O$, and $Na_2CO_3$.

3. A method for preparing a ligand of Formula 2, as depicted in Scheme 2:

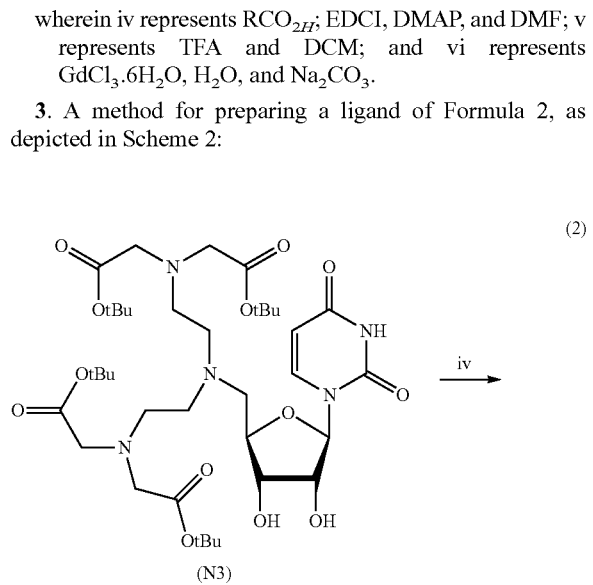
(2)

(N3)

(N4)

20

-continued

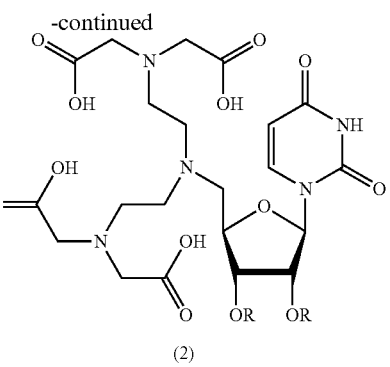
(2)

wherein iv represents $RCO_2H$, EDCI, DMAP, and DMF, and v represents TFA and DCM.

4. The method according to claim 3, wherein the compound of Formula N3 is prepared by Scheme 3:

(3)

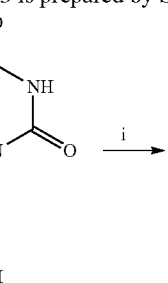

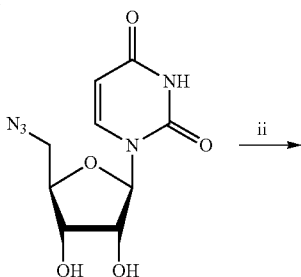
(N1)

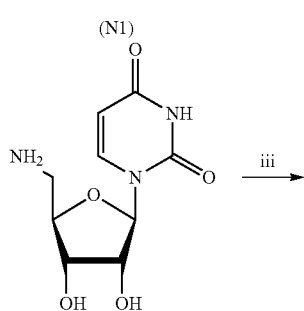
(N2)

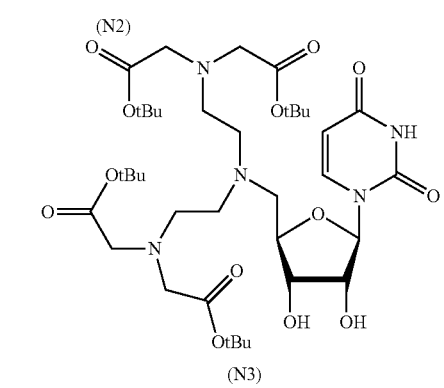
(N3)

wherein i represents $PPh_3$, $NaN_3$, $CBr_4$, and DMF, ii represents $PPh_3$, pyridine then $NH_4OH$, and iii represents N,N-bis[(tert-butoxycarbonyl)methyl]-2-bromoethylamine, $KHCO_3$, and DMF.

\* \* \* \* \*